United States Patent
Ferguson et al.

(10) Patent No.: US 11,559,388 B1
(45) Date of Patent: *Jan. 24, 2023

(54) CONSTRUCTS AND METHODS FOR REPAIRING A TENDON WITH A REDUCED RISK OF REINJURY

(71) Applicant: RIVERPOINT MEDICAL, LLC, Portland, OR (US)

(72) Inventors: Patrick Joseph Ferguson, Portland, OR (US); Patrick Edward Ferguson, Portland, OR (US); Aaron Joseph Sundholm, Portland, OR (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 341 days.

This patent is subject to a terminal disclaimer.

(21) Appl. No.: 16/726,702

(22) Filed: Dec. 24, 2019

Related U.S. Application Data

(63) Continuation of application No. 15/888,541, filed on Feb. 5, 2018, now Pat. No. 10,595,983.

(51) Int. Cl.
*A61F 2/08* (2006.01)
*A61B 17/00* (2006.01)
*A61B 17/06* (2006.01)

(52) U.S. Cl.
CPC .......... *A61F 2/08* (2013.01); *A61B 17/06166* (2013.01); *A61B 2017/00004* (2013.01); *A61B 2017/0618* (2013.01); *A61F 2002/0829* (2013.01); *A61F 2210/0004* (2013.01); *A61F 2250/0031* (2013.01)

(58) Field of Classification Search
CPC ............................... A61B 17/06; A61L 17/00
See application file for complete search history.

(56) References Cited

U.S. PATENT DOCUMENTS

| | | | |
|---|---|---|---|
| 6,296,659 B1 | 10/2001 | Foerster | |
| 6,716,234 B2 | 4/2004 | Grafton et al. | |
| 7,329,271 B2 | 2/2008 | Koyfman et al. | |
| 7,357,810 B2 | 4/2008 | Koyfman et al. | |
| 7,959,650 B2 | 6/2011 | Kaiser et al. | |
| 8,012,172 B2 | 9/2011 | Grafton et al. | |
| 8,088,146 B2 | 1/2012 | Wert et al. | |
| 8,231,654 B2 | 7/2012 | Kaiser et al. | |
| 8,298,284 B2 | 10/2012 | Cassani | |
| 9,737,292 B2 | 8/2017 | Sullivan et al. | |
| 9,757,132 B2 | 9/2017 | Laurencin et al. | |
| 10,595,983 B1 | 3/2020 | Ferguson | |
| 2004/0199208 A1 | 10/2004 | Foerster | |
| 2006/0025818 A1 | 2/2006 | Ferguson et al. | |

(Continued)

FOREIGN PATENT DOCUMENTS

| | | |
|---|---|---|
| EP | 1543848 | 9/2011 |
| WO | 2017171962 A1 | 11/2015 |

*Primary Examiner* — Jason-Dennis N Stewart
(74) *Attorney, Agent, or Firm* — Timothy E. Siegel Patent Law, PLLC; Timothy E. Siegel

(57) ABSTRACT

A tendon repair suture tape comprising a flat braid of elastic, absorbable fibers and high strength fibers, the tape being at least 1 mm wide and 2 cm long, and less than 0.2 mm high. The suture tape includes at least 4 absorbable fibers and at least 4 high strength fibers. Further, the suture tape is capable of being stretched at least 10% from its shortest length to the length at which it breaks, presents an increasing resistance to further stretching as it is stretched, and is capable of withstanding a load of at least 260 Newtons before breaking.

6 Claims, 5 Drawing Sheets

(56) References Cited

U.S. PATENT DOCUMENTS

| | | |
|---|---|---|
| 2006/0155328 A1 | 7/2006 | Foerster |
| 2009/0035572 A1 | 2/2009 | Hotter et al. |
| 2009/0142275 A1 | 6/2009 | Phillips et al. |
| 2009/0143819 A1 | 6/2009 | D'Agostino |
| 2009/0275963 A1 | 11/2009 | May et al. |
| 2011/0098727 A1 | 4/2011 | Kaiser et al. |
| 2011/0251640 A1 | 10/2011 | Lauria |
| 2013/0023927 A1 | 1/2013 | Cassani |
| 2013/0110165 A1 | 5/2013 | Burkhart et al. |
| 2015/0258238 A1 | 9/2015 | Ferguson et al. |
| 2015/0374355 A1 | 12/2015 | Guerra et al. |
| 2017/0055983 A1 | 3/2017 | Bracy |

CONSTRUCTS AND METHODS FOR REPAIRING A TENDON WITH A REDUCED RISK OF REINJURY

RELATED APPLICATIONS

This application is a continuation of application U.S. Ser. No. 15/888,541 filed Feb. 5, 2018, which is incorporated by referenced as if fully set forth herein.

BACKGROUND

Tendon repair surgery typically includes the reinforcement and rejoining of existing tendon tissue, and may include a graft of tendon, from the patient's own body or from another source, such as an animal. It is not unusual in this type of surgery for some portion of the tendon to be reinforced by suture that is sewn into the tendon, repeatedly entering and exiting as the suture extends lengthwise by way of a set of transverse loops. In a technique that is used in both rotator cuff and Achilles tendon repair, in particular where the tendon has ruptured near an anchor point, suture tape in a crossing pattern is used to perform that principal retaining function, acting to replace a portion of the tendon function. In rotator cuff surgery, with the use of round suture, knots are tied, which at the completion of surgery lie directly under the skin, potentially causing patient discomfort. Other problems, such as reinjury, persist. When suture that is not absorbable is used, the lack of elasticity in the suture can cause implanted tendon to tear if the patient flexes too quickly, for example while jumping, in the instance of an Achilles tendon repair. Moreover, permanent suture can cause a subtle disfigurement of the repaired joint and continuing discomfort.

When suture made of absorbable material is used, however, some absorbable material typically is absorbed before robust tissue ingrowth can fully occur. Accordingly, there is a window of vulnerability, when a good portion of the suture is reabsorbed, but the tissue is not in an adequately strong state to support the full strain of, for example, jumping. Many of the absorbable fibers used in partially absorbable sutures are absorbed over a period of about 4 to 6 months, which for many patients is not enough time for adequate recovery.

When reinjury occurs, an entire new surgery is warranted, with the attendant expense. Accordingly, it is very important that tendon repair be provided in a state which quickly becomes and remains, robust.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

The present invention may take the form of a tendon repair suture tape comprising a flat braid of elastic, absorbable fibers and high strength fibers, the tape being at least 1 mm wide and 2 cm long, and less than 0.2 mm high. The suture tape includes at least 4 absorbable fibers and at least 4 high strength fibers. Further, the suture tape is capable of being stretched at least 10% from its shortest length to the length at which it breaks, presents an increasing resistance to further stretching as it is stretched, and is capable of withstanding a load of at least 260 Newtons before breaking.

BRIEF DESCRIPTION OF THE DRAWINGS

Exemplary embodiments are illustrated in referenced drawings. It is intended that the embodiments and figures disclosed herein are to be considered illustrative rather than restrictive.

DETAILED DESCRIPTION OF THE PREFERRED EMBODIMENTS

Figure 1:
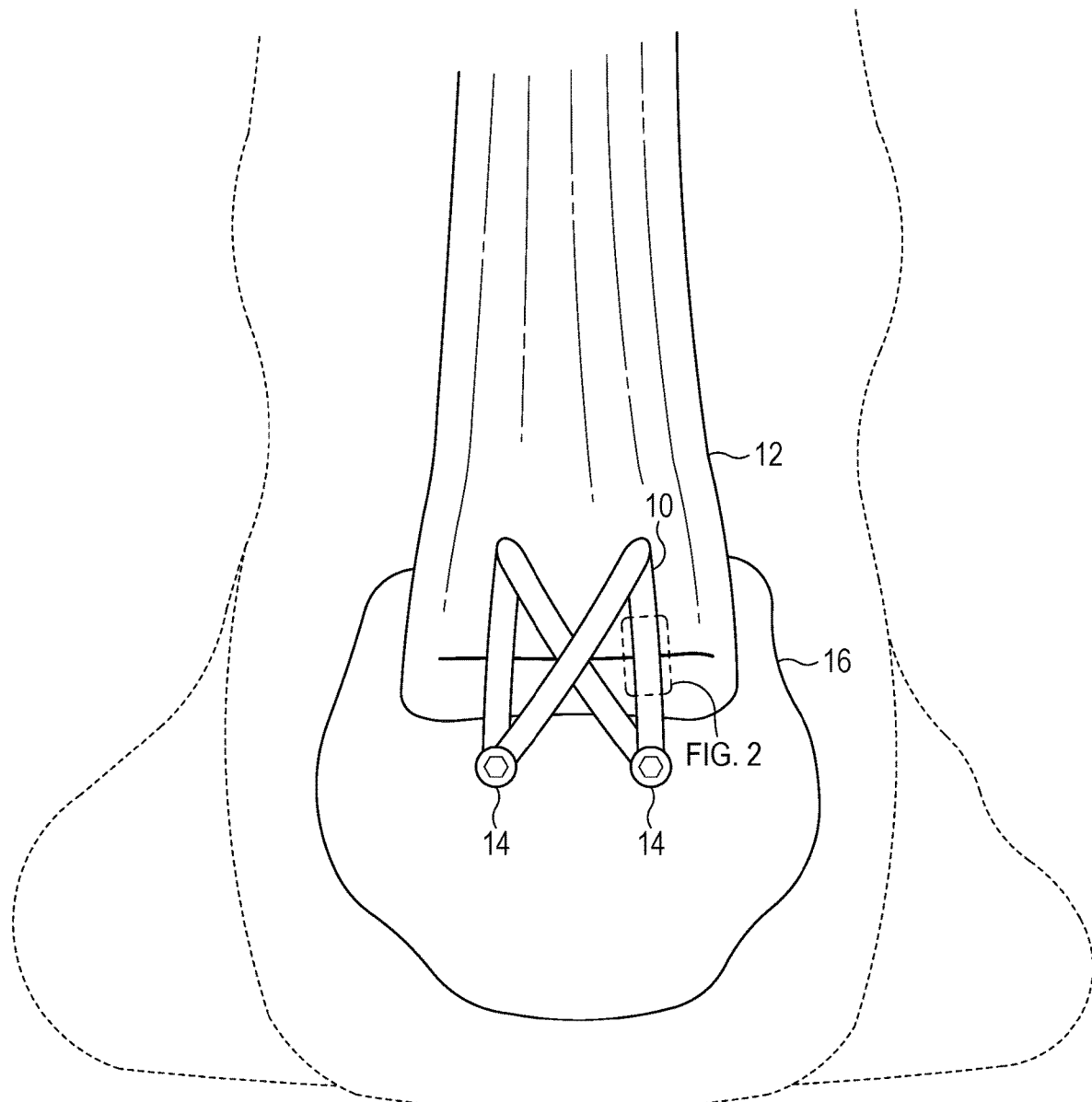
FIG. 1 is an illustration of an Achilles tendon repair using partially absorbable tendon repair suture tape.

The teachings herein are primarily directed to a partially absorbable suture tape and methods of use for such suture tape. FIG. 1 shows partially absorbable suture tape as used in an Achilles tendon repair, as it would appear immediately following completion of the repair surgery. In the repair technique illustrated, the suture tape 10 connects the tendon 12 to screws 14 that are anchored in the bone 16. The suture tape secures the tendon in the desired position in order to facilitate correct and efficient healing. Natural tendon is slightly elastic. Because the suture tape temporarily functions in place of the torn tendon, it is important that the suture tape also be slightly elastic. Using elastic suture tape reduces the probability of the patient suffering a further tendon rupture when the tendon is flexed quickly.

Many differing embodiments of mixed absorbable and high-strength suture tape exist. In embodiments, 4 out of 16; 5 out of 16, 6 out of 16, 7 out of 16, 8 out of 16, 9 out of 16 and 10 out of 16 are absorbable fibers, with the rest being high strength fibers, typically UHMWPE. In other embodiments 8 fibers are used, with the same proportions in differing embodiments, and in another embodiment 32 fibers are used, again with the same proportions in differing embodiments, and with a few more embodiments of 9 out of 32, 11 of 32, 13 of 32, 15 of 32, 17 of 32, and 19 of 32, of absorbable fibers.

Figure 2:
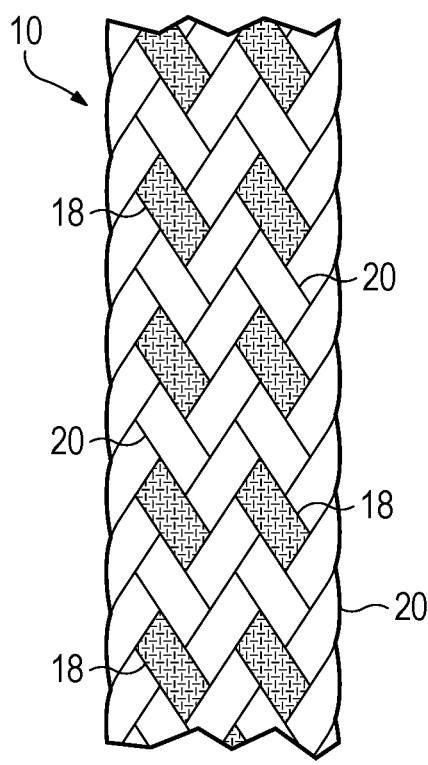
FIG. 2 is a detail view of the partially absorbable tendon repair suture tape.

FIG. 2 shows a detail view of the area indicated in FIG. 1, of suture 10. This detail shows that the partially absorbable suture tape is made up of two different types of fibers. Fibers of absorbable material 18 are braided together with fibers of high strength material 20. In one embodiment, four absorbable fibers are braided together with four high strength fibers. In other embodiments, more than four absorbable fibers are braided together with more than four high strength fibers. The braided structure and materials used result in a suture tape that is both elastic and strong. The suture tape is capable of withstanding a load of at least 260 Newton before breaking. The high strength fibers may be made of any high strength, biocompatible material. In a preferred embodiment, the high strength fibers are ultrahigh molecular weight polyethylene (UHMP). The absorbable fibers may be made of any biocompatible material that retains its structure for a period of time when allowed to remain within a patient's body but is gradually absorbed into the patient's tissues after a longer period of time. In a preferred embodiment, the absorbable fibers are of polybutylene succinate. The absorbable fibers may also be made of other materials, including aliphatic homopolyesters, aliphatic copolyesters, aromatic homopolyesters, aromatic copolyesters, semi-aromatic copolyesters, polyesteramides, polycarbonates, polyanhydrides, polysaccharides, and so forth. Particularly suitable absorbable synthetic polymers may include polycaprolactone, polyesteramides, modified polyethylene terephthalate, polylactic acid and its copolymers, terpolymers based on polylactic acid, polyglycolic acid, polyalkylene carbonates (e.g., polyethylene carbonate, poly(glycolide-co-trimethylene carbonate, etc.), polyhydroxyalkanoates, poly-3-hydroxybutyrate, poly-3-hydroxyvalerate, poly-3-hydroxybutyrate-co-4-hydroybutyrate, poly-3-hydroxybutyrate-co-3-hydroxyvalerate copolymers, poly-3-hydroxybutyrate-co-3-hydroxyhexanoate, poly-3-hydroxybutyrate-co-3-hydroxyoctanoate, poly-3-hydroxybutyrate-co-3-hydroxydecanoate, poly-3-hydroxybutyrate-co-3-hydroxyoctadecanoate, and succinate based aliphatic polymers (e.g., polybutylene succinate, as noted below, polybutylene succinate adipate, polyethylene succinate, etc.). Polybutylene succinate homopolymers and copolymers may be used. Natural absorbable polymers, such as collagen or surgical gut (e.g., chromic or fast absorbing), may also be employed. Examples of suitable non-absorbable, yet biostable materials may include polypropylene, nylon, polyethylene, polyesters (e.g., polyethylene terephthalate), silk, cotton, carbon, steel, and so forth.

Polybutylene succinate (PBS), and many of its copolymers, including PBS adipate (PBSA) and PBS-polylactic acid (PBS-PLA), PBSA-PLA, PBS-talcum, PBS-polybutyrate (PBS-PBAT), PBS-carbon nanotube and PBS-PLA-$CaSO_4$ generally-have the quality of being more slowly absorbed than most other absorbable materials. PBS, specifically typically takes about twelve to fourteen months for absorption, as opposed to about six months, for many other absorbable materials. This can be an advantage as it is sometimes the case that suture material will be absorbed before the natural tendon has grown robust enough to handle a full load, thereby permitting reinjury. Although polylactic acid (PLA) has a similar period of absorption, it is very stiff, lacking the supple quality of PBS, and thereby challenging surgeons using sutures that include fibers of this material. Sutures that include PBS fibers, according to the present invention, include suture tape, and round braids, both with a core and coreless. In differing embodiments, PBS round braid sutures include UPS sizes 0 to 5; 1 to 6; 2 to 7; 3 to 8; 4 to 9, 5 to 10, 0 to 10, 0 to 8 and from 0 to 6. In embodiments, PBS fibers include 2 of 16; 3 of 16, 4 of 16, 5 of 16, 6 of 16, 7 of 16, 8 of 16, 9 of 16 and 10 of 16; also, embodiments of 32 fiber sutures having the above recited proportions (for example, 4 of 32 for 2 of 16), and also proportions of the proportions for 16 fibers, but with an additional PBS fiber, for an odd number of PBS fibers, out of 32 fibers in all.

Polyhydroxyalkanoates (PHS), a class of biocompatible biopolyesters naturally produced by microorganisms, have diverse physical and chemical properties that make them suitable candidates for preparing sutures in accordance to the present invention. In particular, poly(4-hydroxybutyric acid) (Tepha's TephaFLEX® biopolymer; P4HB), a homopolymer of 4-hydroxybutyrate, undergoes complete degradation and resorption between a period of twelve and eighteen months; the 4-hydroxybutyrate resulting from the degradation being quickly metabolized and eliminated by the human body. The long period of degradation and absorption of P4HB, as with the case of PBS, offers the advantage of allowing the injured tissue to sufficiently regenerate before the suture including this material to completely lose its tensile strength. Sutures that include P4HB fibers, according to the present invention, include suture tape, and round braids, both with a core and coreless. In differing embodiments, P4HB round braid sutures include UPS sizes 0 to 5; 1 to 6; 2 to 7; 3 to 8; 4 to 9, 5 to 10, 0 to 10, 0 to 8 and from 0 to 6. In embodiments, P4HB fibers include 2 of 16; 3 of 16, 4 of 16, 5 of 16, 6 of 16, 7 of 16, 8 of 16, 9 of 16 and 10 of 16; also, embodiments of 32 fiber sutures having the above recited proportions (for example, 4 of 32 for 2 of 16), and also proportions of the proportions for 16 fibers, but with an additional P4HB fiber, for an odd number of P4HB fibers, out of 32 fibers in all.

The suture tape is flat in cross-section, allowing it to lie more smoothly below the patient's skin than round suture material. In one embodiment, the suture tape is at least 1 mm wide and 2 cm long, and less than 0.2 mm high. In another embodiment, the suture tape is at least 1 mm wide and 2 cm long, and less than 1 mm high. In one embodiment, the suture tape is between 1 mm and 3 mm wide. In a preferred embodiment, the suture tape is approximately 2 mm wide. In one embodiment, the suture tape is between 2 cm and 100 cm long. In preferred embodiments, the suture tape is 15 cm long, 40 cm long, or 90 cm long.

Figure 3:
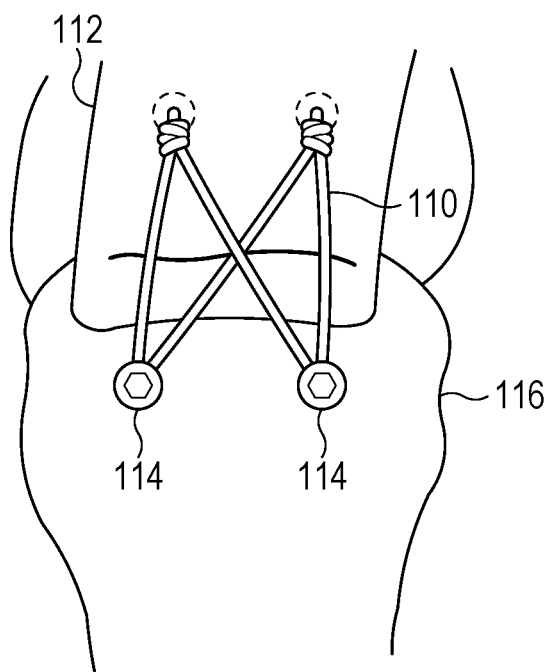
FIG. 3 is an illustration of a rotator cuff repair using partially absorbable tendon repair suture tape.

FIG. 3 shows partially absorbable suture tape as used in a rotator cuff repair. The suture tape 110 connects the tendon 112 with screws 114 that are anchored in the bone 116. The repair technique shown in FIG. 3 is a knotted rotator cuff repair but use of the suture tape is also beneficial in knotless rotator cuff repair techniques. In any tendon repair technique using knots, the flat cross-section of the suture tape is particularly helpful in that the knots can be tied and positioned in such a manner as to lay flat under the patient's skin, reducing the profile height of the knot as compared to round suture material. Surgical knots tied with partially absorbable suture tape typically have at least 10% less height than surgical knots tied with round suture having the same strength. Moreover, as the suture tape is absorbed, the knot becomes less prominent, as the entire suture tape becomes less prominent.

Figure 4:
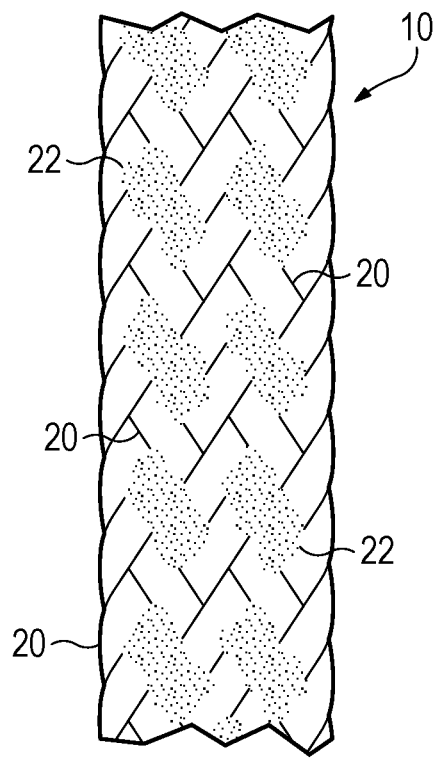
FIG. 4 is a detail view of the partially absorbable tendon repair suture tape showing the ingrowth of the tissue and degradation of the tape as the tape material begins to be absorbed into the tissue.

FIG. 4 shows a detail view of the partially absorbable suture tape at a time following the repair surgery, when the healing process is underway. The absorbable fibers 18, as labeled in FIG. 2, have begun to be absorbed into the patient's tissue and new tissue 22 has begun to grow into and around the suture tape. The high strength fibers 20 remain intact, providing the new tissue with support during the entire healing process.

The mechanical characteristics of the suture tape depend on the width, thickness and composition of the tape. In one preferred embodiment, fibers of an absorbable material are braided together with fibers of ultra-high molecular weight polyethylene (UHMWPE). In one embodiment a mixed braid of 3 fibers of Poly(glycolide-co-caprolactone) (PGCL) are braided with 13 fibers of UHMWPE (each of 215 denier).

Figure 5:
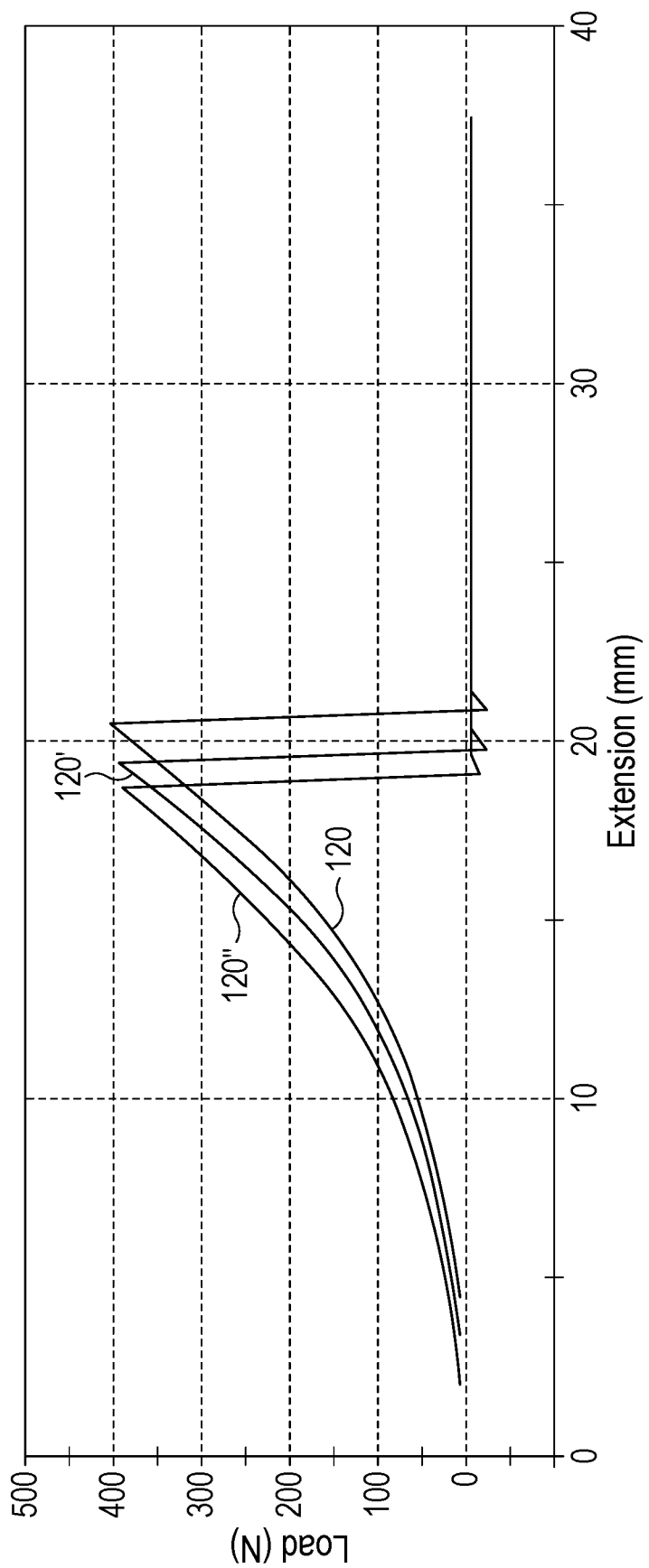
FIG. 5 is a graph of linear extension, versus load needed to produce the linear extension for a 200 mm, 16 strand, 215 denier per strand, flat braid of UHMWPE.
Figure 6:
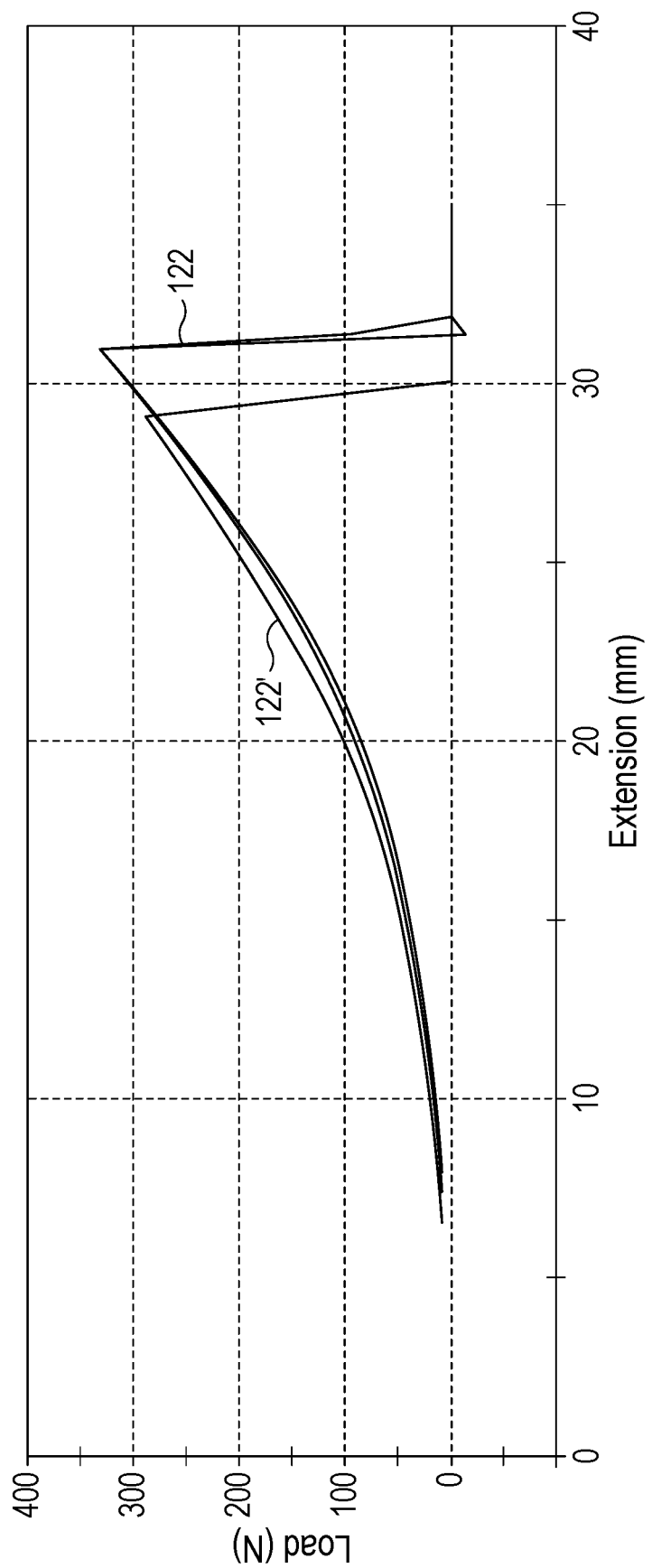
FIG. 6 is a graph of linear extension, versus load needed to produce the linear extension for a 200 mm, 16 strand, 215 denier per strand, flat braid of having 13 strands of UHMWPE and 3 strands of Poly (glycolide-co-caprolactone) (PGCL).

FIG. 5 shows a set of curves 120, 120' and 120" of three tensile strength tests showing elastic extension of a 200 mm pure UHMWPE 16 fiber (each of 215 denier) braid (a "pure braid"), against tensile force in Newtons (the Y-axis). FIG. 6 shows corresponding curves 122 and 122' for the same test but for above described preferred embodiment having a mix of fibers (a "mixed braid"). As can be surmised from a review of FIGS. 5 and 6, the mixed braid can stretch about 1.6 times further than the pure braid, before rupturing, with the mixed braid stretching about 14%, as compared to about 9%, for the pure braid. Although the mixed braid is not as strong as the UHMWPE braid, rupturing about 300 Newtons, as opposed to 400 Newtons, still the chance of a tendon rupture is reduced, due to the increased elasticity, which better accommodates the remaining tendon under repair, which is not placed under as much stress. Further, due to its greater elasticity, the mixed tape will not be placed under as much stress as the pure tape. Typically, the suture or suture tape used in a tendon repair is stronger than is necessary, and the greater danger is a tear in the remaining tendon. Although the UHMWPE fibers are not increased in elasticity, they vary from the original braid pattern as the overall suture is stretched, loosening the pitch of each fiber's helix, so that the overall suture lengthens more, although each fiber of UHMWPE is no more elastic in the mixed braid, than in the pure braid.

Notably, the mixed braid stretches by 20 mm or 10% with less than 100 Newtons of force, while the pure braid requires 400 Newtons of force, but in most instances, breaks before stretching 10%. In other embodiments, with more absorbable fibers added, a mixed braid stretches by 10% with less than 50 Newtons of force applied. The mixed suture stretches 5% with less than 20 Newtons of force applied, whereas the pure braid requires over 50 Newtons of force to stretch 5%.

The desired physical properties of a suture depend on the physical characteristics of the patient, including weight, tendon length and other characteristics of the tendon being repaired. In a preferred method, a medical professional selects a suture from an array of possibilities, based on these qualities. In one method, a repository of sutures is maintained with a wide variety of types having differing features, including elastic profile, percent absorbable, and beginning suture mass, strength, size and physical profile, and parallel characteristics after the absorbable portion is fully absorbed. In one embodiment, the repository services surgeons in an area, rushing the exact suture type requested to the surgeon by delivery or courier service. In one embodiment, the suture repository (and fulfillment center) is accessible by the Internet, with the capability to remotely check inventory, place orders and select delivery options online. In a related embodiment, sutures are made to order, and are selected from a wide range of available physical characteristics. In one embodiment, a computer program is provided that accepts inputs of patient weight, bone and tendon characteristics and outputs a suture type as recommended to use. For example, a woman, weighing 150 lbs., with an Achilles tendon that measures 3 cm in circumference at its midpoint, and having a tibia measuring 40 cm in length, would yield a recommendation of a 16 fiber, 215 denier per fiber suture, with four of the sutures made of polyglycolic acid, and the rest made of UHMWPE.

In embodiments, the suture tape is capable of being stretched at least 10%, 12%, 14% and 16% from its shortest length to the length at which it breaks and presents an increasing resistance to further stretching as it is stretched.

Figure 7:
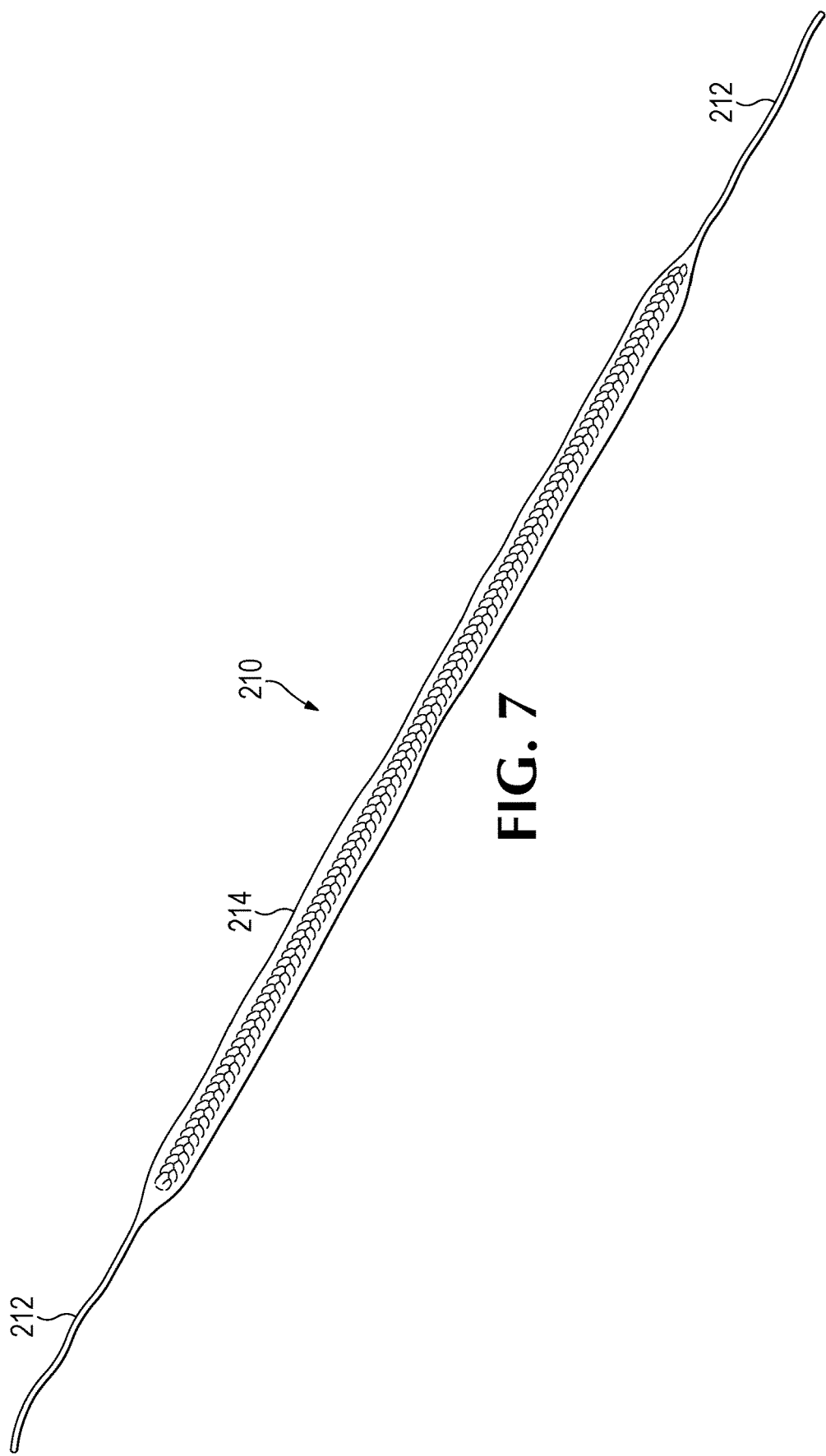
FIG. 7 is an isometric view of a suture tape assembly having two tails, which can be made in accordance with aspects of the present invention.

Referring to FIG. 7, In an additional preferred embodiment, round-flat-round suture tape 210, includes a length of round suture 212, which is preferably a US2 braid, typically formed of eight strands of polyester braided together to form a cover with three to six strands of polyester on the interior. In suture tape 210, suture 212 has been braided as a central warp fiber into a length of flat suture tape 214, with some of the other warp fibers being made of twisted or braided ultrahigh molecular weight polyethylene (UHMWPE) and some of absorbable material, such as PBS and P4HB. Suture 212 extends out of the two ends of suture tape 214, for about 12 inches. Suture tape 214 may be between 3 and 4 feet in length. Because round suture portions 212 are used to pull the tape portion 214 into position, round sutures 212 generally need not be high strength. Other constructions of round-flat-round sutures fall within the scope of the present invention, if they include both fibers of high strength material and fibers of absorbable material.

In an alternative preferred embodiment, a suture 212 that is not of high strength material is used. In the suture art, high strength is sometimes used to denote ultra-high molecular weight polyethylene. Other materials, such as polyester are softer, thereby reducing the chance of cutting into bone after implantation. Polyester also has superior handling qualities. As the tail ends of suture 212 are only used for placement of the tape portion 214 and are typically cut off after tape 212 is implanted, these tail ends do not have to be of high strength material.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A tendon repair suture tape, comprising:
   (a) a flat braid of elastic, absorbable fibers and high strength fibers;
   (b) said tape being at least 1 mm wide and 2 cm long and less than 0.2 mm high;
   (c) including at least 2 absorbable fibers and 4 high strength fibers;
   (d) capable of being stretched at least 10% from its shortest length to the length at which said suture tape breaks, and presenting an increasing resistance to further stretching as it is stretched; and
   (e) capable of withstanding a load of at least 260 Newtons, before breaking.

2. The suture tape of claim 1, wherein said absorbable fibers are made of polybutylene succinate.

3. The suture tape of claim 1, wherein said high strength fibers are made of ultrahigh molecular weight polyethylene.

4. The suture tape of claim 1, wherein said tape is at least 2 mm wide.

5. The suture tape of claim 1, wherein said tape is capable of being stretched between 12% and 20% from its shortest length to the length at which said tape breaks.

6. The suture tape of claim 1, being a 16 fiber braid, of which at least two fibers are of absorbable material.

* * * * *